US00PP08662P

United States Patent [19]

Bringhurst et al.

[11] Patent Number: Plant 8,662

[45] Date of Patent: Mar. 29, 1994

[54] STRAWBERRY PLANT CALLED 'CUESTA'

[75] Inventors: Royce S. Bringhurst; Douglas V. Shaw, both of Davis; Victor Voth, Santa Ana, all of Calif.

[73] Assignee: The Regents of the University of California, Oakland, Calif.

[21] Appl. No.: 41,748

[22] Filed: Apr. 1, 1993

[51] Int. Cl.[5] ..... A01H 5/00

[52] U.S. Cl. ..... Plt./49

[58] Field of Search ..... Plt. 48, 49

*Primary Examiner*—James R. Feyrer

*Attorney, Agent, or Firm*—Townsend and Townsend Khourie and Crew

[57] ABSTRACT

'Cuesta' is a short-day (June-bearing) cultivar similar to 'Chandler' (U.S. Plant Pat. No. 5,262) but with similar or better productivity, larger and more consistent fruit size, and is a more open and less vigorous plant.

2 Drawing Sheets

DESCRIPTION

This invention relates to a new and distinctive short-day type cultivar designated as 'Cuesta', which resulted from a cross performed in 1987 between the cultivar 'Seascape' (U.S. Plant Pat. No. 7,614) and advanced selection Cal 83.25-2 (a hybrid between 'Fern'; U.S. Plant Pat. No. 5,263 and 'Parker'; U.S. Plant Pat. No. 5,267).

'Cuesta' was first fruited at the University of California Wolfskill Experimental orchards near Davis, Calif. in 1988, where it was selected, originally designated Cal 87.109-3, and propagated asexually by runners. Asexual propagules from this original source have been tested at the Watsonville Strawberry Research Facility, University field stations, and to a limited extent in grower fields starting in 1989.

Figure 1:
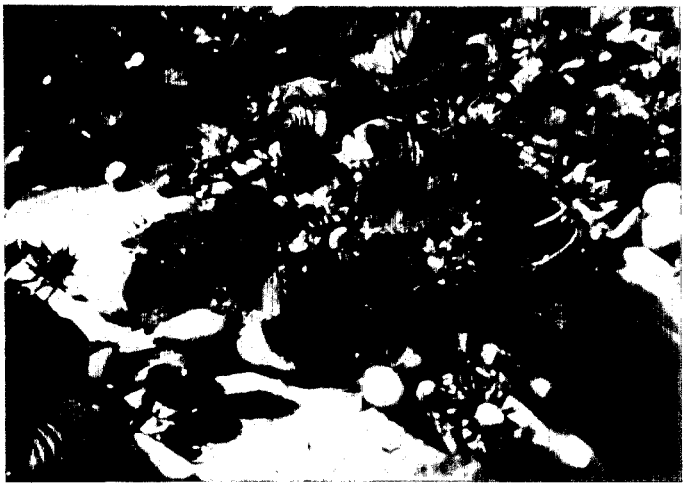
FIG. 1 shows the general flowering and fruiting characteristics of the plant.
Figure 2:
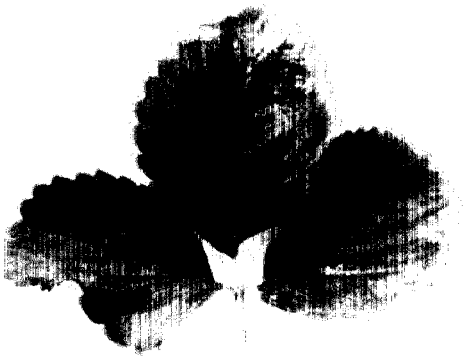
FIG. 2 shows a typical mature leaf during late spring.
Figure 3:
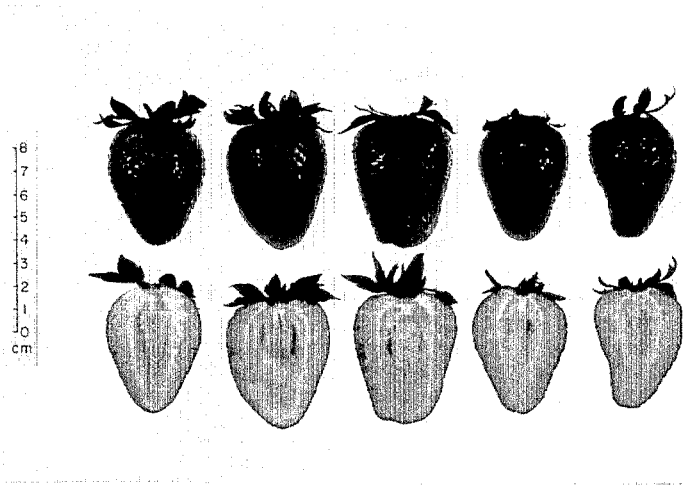
FIG. 3 shows representative midseason fruit.

'Cuesta' is typical of short-day types and produces fruit over an extended period when treated appropriately in cool Mediterranean climates. 'Cuesta' differs from 'Seascape' primarily in that 'Seascape' is a day-neutral genotype whereas 'Cuesta' is a short-day type. Also the production patterns of the two are quite different. The production pattern for 'Cuesta' is similar to that for 'Chandler' (U.S. Plant Pat. No. 5,262), although it produces larger and greater quantities of late-season fruit. 'Cuesta' will be of special interest for winter plantings, where 'Chandler' has been successful, and in summer plantings where 'Pajaro' (U.S. Plant Pat. No. 4,538) has been successful.

Plants and foliage: Fruiting plants of 'Cuesta' are more erect and open than plants of 'Chandler' and generally smaller than either 'Chandler' or 'Oso Grande' (U.S. Plant Pat. No. 6,578). 'Cuesta' forms branch crowns in similar quantity to 'Chandler' with slightly less branching than 'Oso Grande'. When propagated in the nursery, 'Cuesta' has similar runner production capacity to 'Chandler'. Comparative statistics for foliar characters, including leaf color, near mid-season are given for the three cultivars in Table 1, with visual comparisons of leaf color to the Munsell color scale (Nickerson Color Fan) given in Table 5. Leaf color is distinctly lighter on the underside for 'Cuesta'; the differential is similar to 'Chandler' but not as large as for 'Oso Grande'. Leaflets of 'Cuesta' are similar in size to the comparison cultivars, but are somewhat longer and more narrow than for 'Chandler', and are substantially less rounded than for 'Oso Grande'. Leaves (including petioles) are usually shorter than those of 'Chandler'. Petioles are similar in thickness to 'Chandler' and not as thick or stiff as for 'Oso Grande'. Paired stipules, borne in a median position on the petiole, appear as small, stalked, ovate to heart-shaped structures on most leaves for 'Cuesta' and the comparison cultivars. Stipule size varies greatly both within and among individual plants for 'Cuesta', and one or both stipules may be absent or may abscise as the leaf matures. Leaf and petiole pubescence characters for 'Cuesta' are similar to those for 'Chandler', except that tomentum are less dense. Also, leaves for 'Cuesta' are similar in reflectance to those of 'Chandler' but less yellow; leaves for 'Cuesta' are similar in color intensity to 'Oso Grande' but less glossy. Visual comparisons of fruit color according to the Munsell color scale (Nickerson Color Fan) are given in Table 5. 'Cuesta' has concave leaves, similar to or more concave than 'Chandler', and much more concave than leaves of 'Oso Grande'.

Isozymes in leaf extracts: 'Cuesta' has been classified for three isozyme systems using starch gel electrophoresis (Table 2): Phosophoglucoisomerase (PGI), Leucine Aminopeptidase (LAP), and Phosphoglucomutase (PGM). It is distinguishable from all other short-day cultivars released to date except 'Parker'. For electrophoretic procedures see: J. Amer. Soc. Hort. Sci. 106:684–687.

Disease and pest reaction: 'Cuesta' is moderately susceptible to common leaf spot (*Ramularia tulasnei*) and powdery mildew (*Sphaerotheca macularis*). When treated properly, it has tolerance to two-spotted spidermites (*Tetranychus urticae*) that is comparable with that of 'Chandler'. 'Cuesta' is tolerant to strawberry viruses encountered in California.

TABLE 1

Foliar characteristics for 'Cuesta', 'Chandler', and 'Oso Grande'.

| | Cultivar | | |
|---|---|---|---|
| Foliar Character | 'Cuesta' | 'Chandler' | 'Oso Grande' |
| Mid-tier leaflet | | | |
| Length (mm) | | | |
| mean | 84.0 | 82.4 | 77.2 |
| range | 74–96 | 78–94 | 75–80 |

TABLE 1-continued

Foliar characteristics for 'Cuesta', 'Chandler', and 'Oso Grande'.

| Foliar Character | Cultivar 'Cuesta' | 'Chandler' | 'Oso Grande' |
|---|---|---|---|
| Width (mm) | | | |
| mean | 66.8 | 71.4 | 67.6 |
| range | 52–77 | 63–88 | 62–71 |
| Mid-tier leaf | | | |
| Length (mm) | | | |
| mean | 218.0 | 244.2 | 191.6 |
| range | 205–228 | 218–262 | 170–200 |
| Width (mm) | | | |
| mean | 137.4 | 148.0 | 137.2 |
| range | 117–154 | 132–158 | 130–149 |
| Leaf color (CIELAB)* | | | |
| L* | | | |
| mean | 31.2 | 31.4 | 31.9 |
| range | 28.6–34.2 | 27.1–33.3 | 29.9–33.0 |
| a* | | | |
| mean | −5.5 | −8.0 | −5.3 |
| range | −3.8––6.8 | −5.2––8.2 | −4.2––8.3 |
| b* | | | |
| mean | 14.4 | 16.0 | 15.5 |
| range | 12.4–16.7 | 12.9–21.4 | 12.5–20.6 |
| # leaflets/leaf | 3 | 3 | 3 |
| Leaf convexity | concave | concave | concave |
| Serrations | | | |
| number | many | many | moderate |
| shape | semi-pointed | semi-pointed | semi-round |
| Leaf pubescence | sparse | moderate/ sparse | moderate/ heavy |
| Petiole pubescence | | | |
| density | sparse | heavy | heavy |
| direction | perpendicular | acropetal | perpendicular |

*CIELAB is the abbreviation of the international color system known as "Commission Internationale De L'Eclairage" 1978. Recommendations on uniform color spaces — color difference equations, psychometric color terms, Supplement No. 2 to CIE Publication No. 15. PARIS.

TABLE 2

Isozyme phenotypes for 'Cuesta', 'Chandler', and 'Oso Grande'.

| Locus | Cultivar 'Cuesta' | 'Chandler' | 'Oso Grande' |
|---|---|---|---|
| PGI | A4 | A1 | A2 |
| LAP | B3 | B3 | B3 |
| PGM | C2 | C1 | C2 |

Flowering, fruiting, fruit, and production characteristics: 'Cuesta' is similar to 'Chandler' in its production pattern, and produces more early fruit at Watsonville than 'Oso Grande' (with conventional winter planting). Comparative statistics for flower and fruit characters, including fruit color, near mid-season are given for the three cultivars in Table 3. The primary flowers for 'Cuesta' are similar in size to 'Chandler' and 'Oso Grande', whereas the sepals are somewhat larger than for the comparison cultivars; each primary flower has 5–6 petals. The calyx for 'Cuesta' is usually even with the shoulder of the fruit; early-season fruit can have a slight neck. The fruit shape for 'Cuesta' is a long conic, and is easily distinguished from 'Chandler' (flat conic) and 'Oso Grande' (rounded or block conic). External fruit color for 'Cuesta' is slightly darker and less glossy than for 'Chandler' and 'Oso Grande'; internal color is darker than 'Chandler' and substantially darker than for 'Oso Grande'. Achenes vary from light red to dark red, and are even with the fruit surface or slightly indented.

'Cuesta' has been tested under a variety of cultural regimes, and optimal performance is obtained when nursery treatments, pre-plant chilling regimes, plant densities, and nutritional programs similar to those that optimize performance for 'Chandler' are used. In general, 'Cuesta' is less sensitive to over-chilling than 'Chandler'.

When treated with appropriate planting regimes, 'Cuesta' has larger fruit and produces greater yields than 'Chandler' (Table 4); 'Cuesta' has greater yield and produces fruit similar in size to fruit from 'Oso Grande'. Commercial appearance ratings have been equal to or better than those for 'Chandler'. Fruit firmness is similar to that for 'Chandler' but 'Cuesta' is not as firm as 'Oso Grande'. Subjectively, 'Cuesta' has very good flavor, somewhat less aromatic than 'Chandler', less sweet but better balanced than for 'Oso Grande'. The fruit will be acceptable for fresh market, will be exceptional for processing, due to its internal color and will be useful for home garden purposes.

TABLE 3

Flower and fruit characters for 'Cuesta', 'Chandler', and 'Oso Grande'.

| Character | Cultivar 'Cuesta' | 'Chandler' | 'Oso Grande' |
|---|---|---|---|
| # petals | | | |
| mean | 6.5 | 6.6 | 5.0 |
| range | 5–6 | 6–8 | 5–5 |
| Flower position (relative to foliage) | even/ slightly interior | even/ exposed | exposed |
| Calyx diam. (mm) | | | |
| mean | 60.0 | 47.7 | 34.1 |
| range | 50–68 | 45–53 | 27–38 |
| Corolla diam. (mm) | | | |
| mean | 41.0 | 39.3 | 32.2 |
| range | 38–46 | 36–46 | 27–41 |
| Fruit shape | | | |
| length/width ratio | 1.32 | 1.33 | 1.06 |
| subjective | conic | flat conic | blocky/conic |
| Calyx position | even | even/slight neck | even/slight indent |
| Seed position | even/slight indent | even/slight indent | even |
| Fruit color (CIELAB) | | | |
| external | | | |
| L* | 21.7 | 23.6 | 22.4 |
| a* | 26.3 | 38.5 | 31.2 |
| b* | 14.7 | 14.8 | 17.2 |
| internal | | | |
| L* | 39.9 | 46.2 | 54.1 |
| a* | 41.2 | 39.1 | 30.4 |
| b* | 33.2 | 29.4 | 22.7 |

TABLE 4

Performance for selection 'Cuesta' compared with 'Oso Grande' and 'Chandler' at the Watsonville Research Facility for the 1991 trial. All plants were dug from a nursery near MacDoel, CA on October 5, 1990.

| | Weeks storage | Yield (g/plant) | Size (g/fruit) | Appearance Score | Firmness |
|---|---|---|---|---|---|
| 'Cuesta' | 1 | 1,906 | 24.4 | 4.0 | 7.2 |
| | 3 | 2,274 | 27.8 | 4.2 | 7.4 |
| 'Chandler' | 1 | 1,647 | 23.2 | 3.8 | 6.8 |
| | 3 | 2,078 | 25.8 | 4.0 | 7.1 |
| 'Oso Grande' | 1 | 1,237 | 25.7 | 3.7 | 8.0 |
| | 3 | 1,740 | 27.1 | 3.8 | 8.3 |

TABLE 5

Munsell color classification for leaf and fruit characters.

| Item | Munsell Leaf Color Classes Upper (Adaxial) | Munsell Leaf Color Classes Lower (Abaxial) | Munsell Fruit Color Classes External | Munsell Fruit Color Classes Internal |
|---|---|---|---|---|
| Chandler | 5GY 4/3 | 5GY 5/6 | 5R 5/13 | 7R 5/13 |
| | 5GY 5/6 | | 5R 4/12 | |

TABLE 5-continued

Munsell color classification for leaf and fruit characters.

| Item | Munsell Leaf Color Classes Upper (Adaxial) | Munsell Leaf Color Classes Lower (Abaxial) | Munsell Fruit Color Classes External | Munsell Fruit Color Classes Internal |
|---|---|---|---|---|
| Oso | 5GY 4/3 | 5GY 5/6 | 5R 5/13 | 7.5R 7/9 |
| | 5GY 3/2 | 7.5GY 6/8 | 7.5R 5/13 | 7.5R 6/12 |
| Cuesta | 7.5GY 6/8 | 10GY 7/8 | 5R 4/12 | 7.5R 5/13 |
| | | | 5R 3/7 | 7.5R 4/11 |

We claim:

1. The new and distinct variety of strawberry plant illustrated and described and having the characteristics above enumerated.

* * * * *